United States Patent
Downey et al.

(10) Patent No.: US 6,228,018 B1
(45) Date of Patent: May 8, 2001

(54) REMOVABLE LEFT VENTRICULAR ASSIST DEVICE WITH AN AORTIC SUPPORT APPARATUS

(75) Inventors: H. Fred Downey; Xiaoming Bian, both of Fort Worth, TX (US)

(73) Assignee: My-Tech, Inc., Tampa, FL (US)

( * ) Notice: Subject to any disclaimer, the term of this patent is extended or adjusted under 35 U.S.C. 154(b) by 0 days.

(21) Appl. No.: 09/245,633

(22) Filed: Feb. 5, 1999

(51) Int. Cl.⁷ ........................................... A61M 1/10
(52) U.S. Cl. ................................. 600/18; 623/3.1
(58) Field of Search ................... 600/16–18; 623/3.1, 623/3.16, 3.21, 3.26, 3.28

(56) References Cited

U.S. PATENT DOCUMENTS

| | | | |
|---|---|---|---|
| 4,407,271 | * 10/1983 | Schiff | 600/17 |
| 4,515,587 | 5/1985 | Schiff | 604/96 |
| 4,527,549 | * 7/1985 | Gabbay | 600/18 |
| 4,697,574 | 10/1987 | Karcher et al. | 128/1 D |
| 4,861,330 | * 8/1989 | Voss | 600/18 |
| 4,902,272 | * 2/1990 | Milder et al. | 600/18 |
| 4,969,458 | 11/1990 | Wiktor | 606/194 |
| 5,151,105 | 9/1992 | Kwan-Gett | 623/1 |
| 5,167,628 | 12/1992 | Boyles | 604/101 |
| 5,287,861 | 2/1994 | Wilk | 128/898 |
| 5,409,444 | 4/1995 | Kensey et al. | 600/18 |
| 5,755,687 | 5/1998 | Donlon | 604/53 |
| 5,782,906 | 7/1998 | Marshall et al. | 623/1 |

OTHER PUBLICATIONS

Patrick M. McCarthy et al., Cardiopulmonary Support and Physiology, 115 J. Thoracic Cardiovascular Surgery 904 (1998).

\* cited by examiner

*Primary Examiner*—Kennedy Schaetzle
(74) *Attorney, Agent, or Firm*—Charles D. Gunter, Jr.

(57) ABSTRACT

An apparatus and method of temporarily replacing the function of the left ventricle in a patient whose heart is severely injured and is unable to maintain a systemic arterial pressure adequate to support the inside walls of patient's aorta, the method comprising a removable pressurizable support means having an external profile which is expandable to fit firmly against the inside wall of the aorta of a patient, wherein the external profile of the pressurizable support means presents a central opening that allows blood to flow through the aorta. The pressurizable support means can both support and expand the aorta under low blood pressure to assist the drawing of blood from the left ventricle. The central opening also allows for the placement of a blood flow control means. The blood flow control means can comprise a pumping balloon and a proximal blocking balloon, the two members pressurized and depressurized in opposition within the aorta of a patient to simulate systole and diastole of a healthy heart. The pumping balloon has a pressurized pumping position that is engaged while the proximal blocking balloon is in a depressurized deflated position.

28 Claims, 5 Drawing Sheets

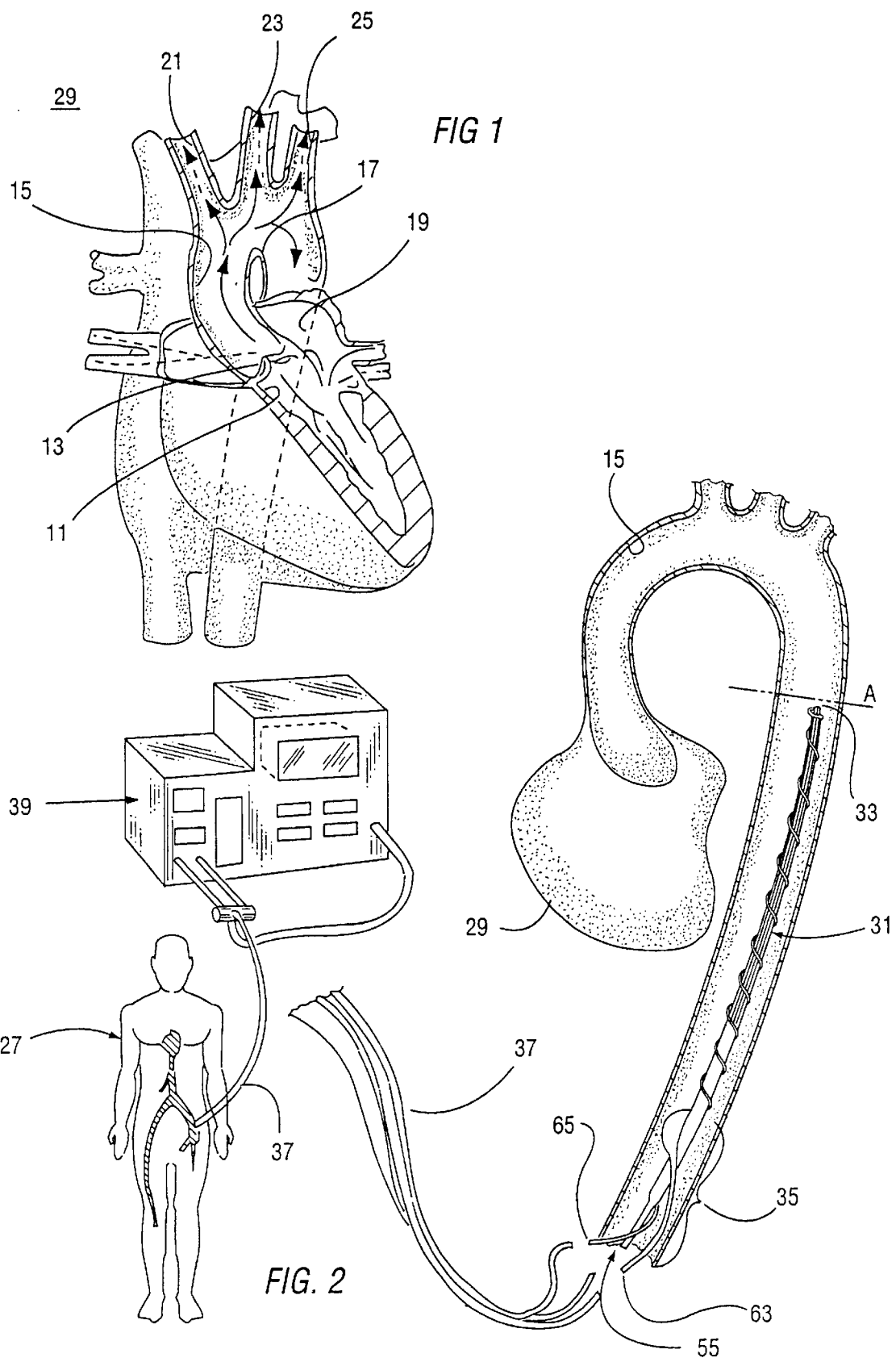

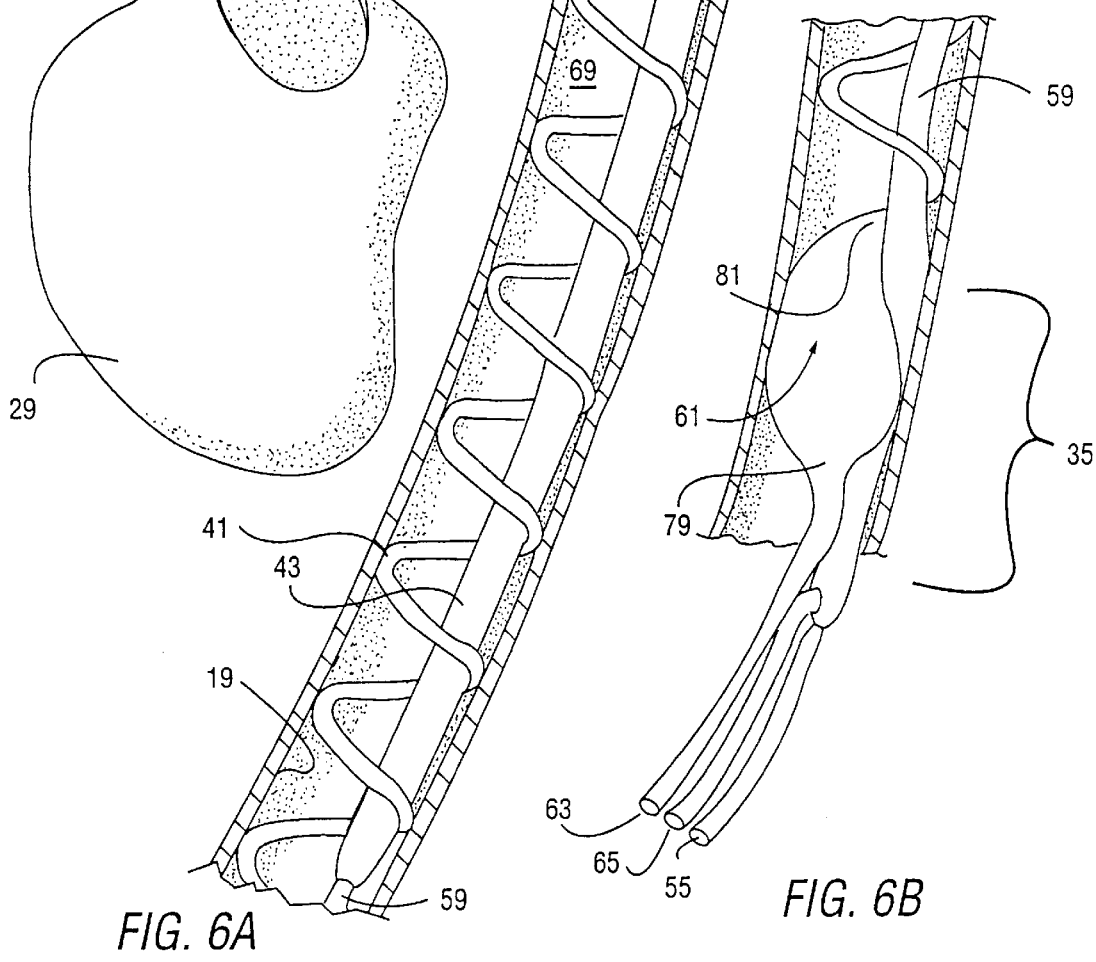
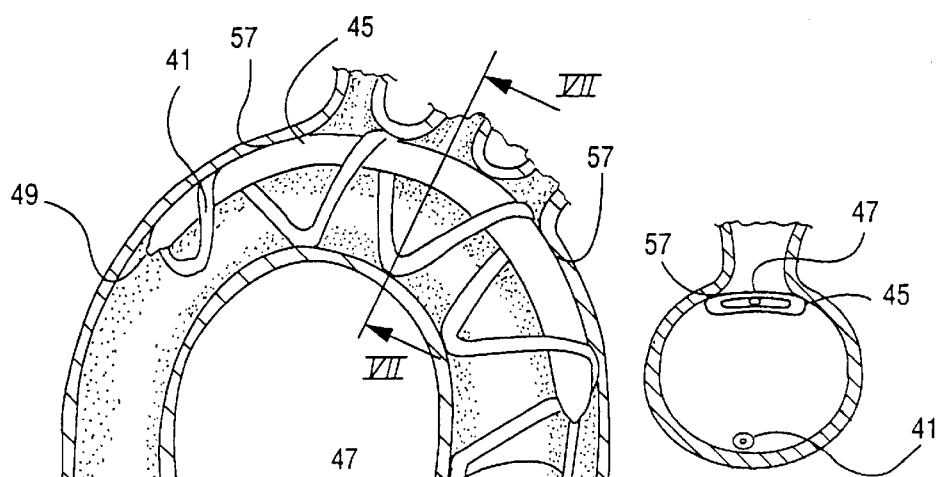
FIG. 6A  FIG. 6B  FIG. 7

REMOVABLE LEFT VENTRICULAR ASSIST DEVICE WITH AN AORTIC SUPPORT APPARATUS

BACKGROUND OF THE INVENTION

1. Field of the Invention

The present invention relates in general to a left ventricular assist device, and in particular to an apparatus and method for supporting the blood circulation when the heart is severely injured and is unable to maintain a systemic arterial pressure adequate to support the inside walls of patient's aorta. Still more particularly, the present invention relates to an apparatus and method for supporting and expanding the walls of the aorta from collapse during operation of the device, which might otherwise occur due to extremely low blood pressure and for providing diastole/systole-like cardiac function in a patient with a severely diseased or injured heart.

2. Description of the Prior Art

In the United States alone, 60,340,000 people have cardiovascular disease. Of these, over 2,000,000 have congestive heart failure, with more than 500,000 new cases diagnosed each year. In 1995, only 2,359 patients received heart transplants, the most permanent of treatments to date, while 770 patients who qualified for heart transplant died waiting. About 450,000 patients undergo open-heart surgery each year, and 2% of these cases require mechanical cardiac support after surgery at a cost of about $400,000 per survivor.

There are many different causes of heart failure, the most common of which are (1) acute myocardial infarction; (2) cardiomyopathy; (3) cardiac valvular dysfunction; (4) extensive cardiac surgery; and (5) uncontrolled cardiac arrhythmias. Heart failure, especially resulting from disease or damage to the left ventricle of the heart, can result in many problems.

Problems arising from left ventricle disfunction are particularly troublesome since the heart itself, as well as the rest of the body, depends on left ventricle function for oxygenated blood to maintain aerobic respiration. Heart failure results in ineffective emptying of the failing left ventricle during systole, which can result in (1) decreased cardiac output; and (2) elevated left atrial and pulmonary venous pressures, which cause pulmonary congestion and edema. Pulmonary congestion and edema, or tissue swelling, prevent effective oxygenation of the arterial blood, and coupled with reduced cardiac output, and can lead to tissue hypoxia. In the final stage of congestive heart failure, a vicious cycle leads to progressive systemic hypotension (low blood pressure), hypoxemia (oxygen depletion), tissue anoxia, further depression of cardiac function and cardiac arrhythmias, and ultimately, death.

Left ventricular assist devices (LVAD) are an alternative treatment for heart failure to transplantation or medical therapy. Patrick M. McCarthy et al., Cardiopulmonary Support and Physiology, 115 J. Thoracic Cardiovascular Surgery 904 (1998). LVADs that are presently available in clinical settings or being developed are of several types: (1) the heart-lung machine, providing cardiopulmonary bypass; (2) intra-aortic balloon pumps (IABP), which reduce resistance to left ventricular ejection and augment diastolic pressure; (3) pumps positioned in parallel with the left ventricle; and (4) complete artificial hearts. Of these, only the IABP devices can be implemented without surgically opening the chest and operating on the heart and/or major blood vessels. Further, after improvement of left ventricular function, only the IABP devices can be removed without opening the chest and operating on heart and blood vessels. Thus, this device has become, by far, the most commonly utilized LVAD. However, the application of present IABP devices is limited to less severecases, since the IABP can function effectively only if the left ventricle is able to eject an adequate output to maintain a mean systemic arterial pressure greater than 60 mmHg. This greatly limits the practical use of present IABPs.

When the heart is injured to the point that mean systemic arterial pressure is less than 60 mmHg, the aorta will collapse during the deflation phase of present IABPs. There are no prior art devices that can be used to support the walls of the aorta so that the IABP can effectively assist heart function. Some stent devices have been used to mechanically support smaller arteries, especially the coronary arteries. But these devices are permanently placed within smaller arteries, and are not designed to be used in conjunction with other devices placed within the artery that assist in increasing systemic arterial blood pressure. There is yet a need for a device that can be used to support the aorta, can be used in conjunction with IAPBs, and is removable. With such a device, blood can be sucked from the defective left ventricle and then pumped to the systemic circulation, essentially replacing the function of a severely injured heart.

Therefore, the present invention is directed towards a LVAD device that can act as a temporary replacement for the function of the left ventricle in a patient whose heart is severely diseased or injured and is unable to maintain a systemic arterial pressure adequate to support the aorta, as required for effective operation of present IABPs.

SUMMARY OF THE INVENTION

It is therefore one object of the present invention to provide an apparatus and method for temporarily replacing the function of the left ventricle in a patient who is suffering severe heart disease or trauma.

It is another object of the present invention to provide an apparatus and method for temporarily providing support to the inside aortic walls of a patient who is suffering from severe heart disease or trauma, such that the left ventricle is unable to maintain enough systemic arterial pressure to prevent the collapse of the walls of the aorta during use of an IABP.

Another object of the present invention is to expand the walls of the aorta during the ejection phase of the left ventricle, so as to enhance ejection of blood from the left ventricle into the aorta. This expansion of the aorta is synchronized with inflation of blocking balloons to prevent reflux of blood from arteries of the aortic arch and from the distal aorta and is also synchronized with deflation of a pumping balloon or blood flow control means positioned in the descending aorta.

It is another object of the present invention to provide an apparatus and method for creating an intermittent elevation of aortic blood pressure, so as to perfuse the systemic circulation with oxygenated blood in a patient who has suffered severe heart disease or trauma such that the left ventricle is not functioning or is functioning only minimally.

It is another object of the present invention to provide an apparatus and method for blocking the flow of blood to the aortic arch arteries during left ventricle systole and concomitant deflation of the device's pumping balloon, so that backflow of oxygenated blood from the aortic arch and from the distal aorta will not reduce the efficiency of the pumping-function of the device.

It is another object of the present invention to provide a cost-effective and easily operated LVAD and aortic support and expansion capabilities that can be placed within the aorta of a patient by insertion through a femoral artery, as would be accomplished with a typical intra-aortic catheter.

The foregoing objects are achieved through a ventricular assist device with aortic supporting and expanding capability and method comprising a removable, pressurizable support means positionable within the aorta of a patient, the pressurizable support means having an external profile which is expandable to fit firmly against the inside wall of the aorta of a patient and to intermittently expand the aorta during the ejection phase of the left ventricle. The external profile also presents a central opening that allows blood to flow through the aorta while a pumping balloon and distal blocking balloon are deflated. A pressure control port is coupled to the removable pressurizable support means which carries the pressurization gas from a pressurization control means external to the patient.

Other devices are placed within the central opening of the pressurizable support means. A blood flow control means provides a surge of oxygenated blood to the systemic arterial circulation within the central opening of the pressurizable support means. The blood flow control means in the embodiment of this invention is a pumping balloon having a pumping position when pressurized, and a sucking position when depressurized. A lumen tube is coupled to the pumping balloon which carries the pressurization gas from a pressurization control means, the pressurization control means being located outside the patient.

An extendable-semirigid tube passes through the center of the pumping balloon and through the center of the proximal blocking balloon. This tube provides positional support for the proximal blocking balloon, and has a pressure sensing port at its proximal end. The distal end of the extendable-semirigid tube serves as a means for the practitioner to maneuver the apparatus within the aorta for proper placement. The preformed extendable-semirigid tube has a proximal and distal end, the proximal end being inserted towards the ascending portion of the aorta, and the distal end of the extendable-semirigid tube being coupled to a means for sensing the pressure within the aorta.

Two blocking balloons are also provided—the distal blocking balloon and proximal blocking balloon—having blocking positions when pressurized, and deflated positions when depressurized. The purpose of the distal blocking balloon is to block retrograde flow of blood coming from the descending aorta while the pumping balloon is in its sucking position. The distal blocking balloon functions by fitting against the inside wall of the descending aorta distal to the pumping balloon while in its blocking position. The distal blocking balloon is in the blocking position when the pumping balloon is in the sucking position. The distal blocking balloon is in a deflated position when the pumping balloon is in the pumping position, thus allowing blood to flow past the deflated balloon into the descending aorta and throughout the patient.

The proximal blocking balloon is pressurized to its blocking position when the pumping balloon is in the sucking position. The proximal blocking balloon is placed at the entrance to the aortic arch arteries and blocks blood flow to these arteries when pressurized. The proximal blocking balloon is depressurized to its deflated position when the pumping balloon is in its pumping position, thus allowing blood to flow past the deflated balloon into the aortic arch arteries. The distal blocking balloon pressurization gas is supplied through a pressure control port which is connected to the distal blocking balloon, the pressurizable support means, and the proximal blocking balloon.

The apparatus is placed in the aorta of a patient through a two stage catheterization procedure. In the first stage of the procedure the apparatus is inserted within the aorta in a deflated (depressurized) and non-extended position, the proximal blocking balloon being held within the inner bore of the pumping balloon support tube. In the second stage of the insertion procedure, the proximal blocking balloon is pushed into a position within the aortic arch, thus able to block the aortic arch arteries when pressurized, while allowing blood flow when depressurized. The apparatus is in a depressurized state while inserting.

Additional objects, features and advantages will be apparent in the written description which follows.

BRIEF DESCRIPTION OF THE DRAWINGS

FIG. 1 is a cutaway diagram of the human heart showing the flow of blood from the left ventricle;

FIG. 2 is a generalized diagram and cutaway view of the apparatus being placed in an aorta of a patient and being coupled to the pressurization control means;

FIG. 6A is a cutaway view of the apparatus within the aorta of a patient, the pumping balloon in the depressurized sucking position, and the support means is in the expanded position; and FIG. 6B is a cutaway view of the distal blocking balloon of the device in the pressurized blocking position;

FIG. 7 is a cross-section taken from FIG. 6A at VIII—VIII showing the pressurized blocking position of the proximal blocking balloon;

DESCRIPTION OF THE INVENTION

Figures 3, 4:
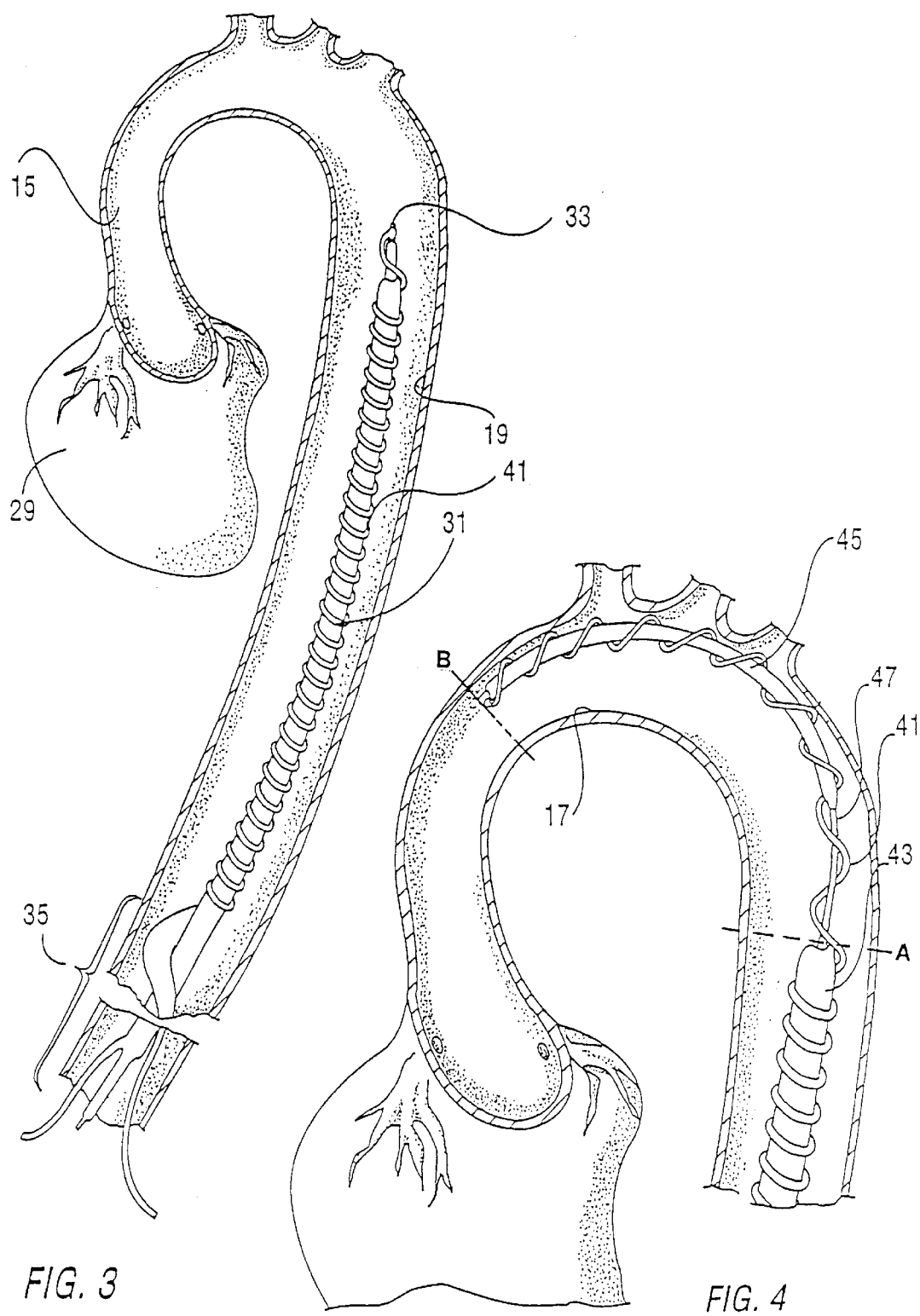
FIG. 3 is a close-up cutaway view of the apparatus in the first stage of insertion in the aorta of a patient.
FIG. 4 is a close-up cutaway view of the apparatus in the second stage of insertion in the aorta of a patient.

The present invention provides a dual function. The first is to provide a removable, pressurizable means of support and expansion of the inside walls of the aorta, in particular the aortic arch and descending portions of the aorta. In conjunction with this function, the present invention provides a LVAD using a blood flow control means that can be placed within the aorta simultaneous to and in conjunction with having the support means within the aorta. It is these two functions of the invention that allow its use in the aorta of a patient whose heart condition is such that presently available IABP devices are useless. The dual purpose of the present invention is shown in the preferred embodiment described below.

A partial cutaway view of the human heart 29 is shown in FIG. 1. The left ventricle 11 is where oxygenated blood coming from the lungs is pumped into the body. The aortic valve 13 controls the flow of blood, opening during the systole phase of the heart's cycle and closing during the diastole phase. Oxygenated blood exits into the ascending aorta 15 in the direction of the arrows shown in FIG. 1. The blood can then flow to the aortic arch 17, coronary arteries, the descending aorta 19 (shown partially in dotted lines), and aortic arch arteries: the left subclavian artery 25, the left common carotid artery 23, and the brachiocephalic trunk 21.

A general schematic diagram of the inserted, depressurized and non-extended LVAD, hereinafter "apparatus," is shown in FIG. 2. The patient 27 who is suffering from severe heart trauma or disease is treated with the apparatus, one embodiment of which is shown at 31. A close up view of the patient's heart 29 and aorta shows the apparatus 31 being inserted, with the apparatus in the insertion position such that all parts are depressurized. The proximal end 33 of the apparatus is inserted first, and the distal end 35 is inserted last. Coupled to the distal end 35 of the apparatus by tube sheath 37 is the pressurization control means 39, which controls the flow of pressurization gas into (pressurization) and out of (depressurization) the apparatus 31 through external pressure control tubes 63 and 65.

Pressure sensing port 55 extends from the distal end of the extendable-semirigid tube 47, port 55 being coupled to the external pressure transducer. The port 55 is continuous with and part of the tube 47, extending from the lumen sheath 59. The separate external lumen tubes 63 and 65 are coupled to the distal end of the apparatus and carry the pressurization gas, typically helium, into and out of the distal blocking balloon, pressurizable support means, and proximal blocking balloon (tube 63) and pumping balloon (tube 65).

Insertion of Apparatus in Aorta

The method of insertion of the apparatus into the aorta of a patient is now described. FIG. 3 and FIG. 4 show a close-up view of the insertion of apparatus 31 into the patient. These figures represent one embodiment of the apparatus 31 and its method of insertion into the patient. FIG. 3 shows the first stage insertion of the apparatus, the apparatus being in the depressurized and non-extended position. The proximal end 33 of the apparatus is at position A. The pressurizable support means, which in this case is an inflatable coil 41, is in the insertion position (depressurized state). The inflatable coil, pumping balloon, and distal and proximal blocking balloons are made of an inflatable material that, when pressurized with gas, will expand, and when depressurized, will contract or collapse.

FIG. 4 shows the second stage insertion of the apparatus 31. In the second stage of insertion, the apparatus is in an extended position. A proximal blocking balloon 45 is now advanced into the aortic arch 17 region to position B. The pumping balloon 43 remains at the position A, and both the pumping and proximal blocking balloons are in the depressurized state. The pumping balloon 43 and proximal blocking balloon 45 are inflatable tubes or balloons whose operation will be described more fully hereafter. Extendable-semirigid tube 47 runs longitudinally through the device from the proximal end 33 beginning at opening 49 (See FIG. 5A and 5B) to the distal end 35 ending in pressure control port 55. The proximal end 49 of the extendable-semirigid tube is open and acts as a pressure sensing port, the tube having an internal bore running continuously to the proximal end 55 of tube 47. The tube 55 is ultimately coupled to an external pressure transducer that will provide information on the pumping function of the apparatus. The electrocardiogram triggers the pressurization control means 39, thereby pressurizing and depressurizing the balloons of the device. The extendable-semirigid tube 47 can also be used to inject substances into the patient's central arterial circulation. Further, the extendable-semirigid tube is made in a preformed shape and of strength such that the medical practitioner inserting the apparatus into a patient's aorta can apply force to the tube at end 55 to install and position the apparatus against the arch of the aorta.

Figures 5A, 5B:
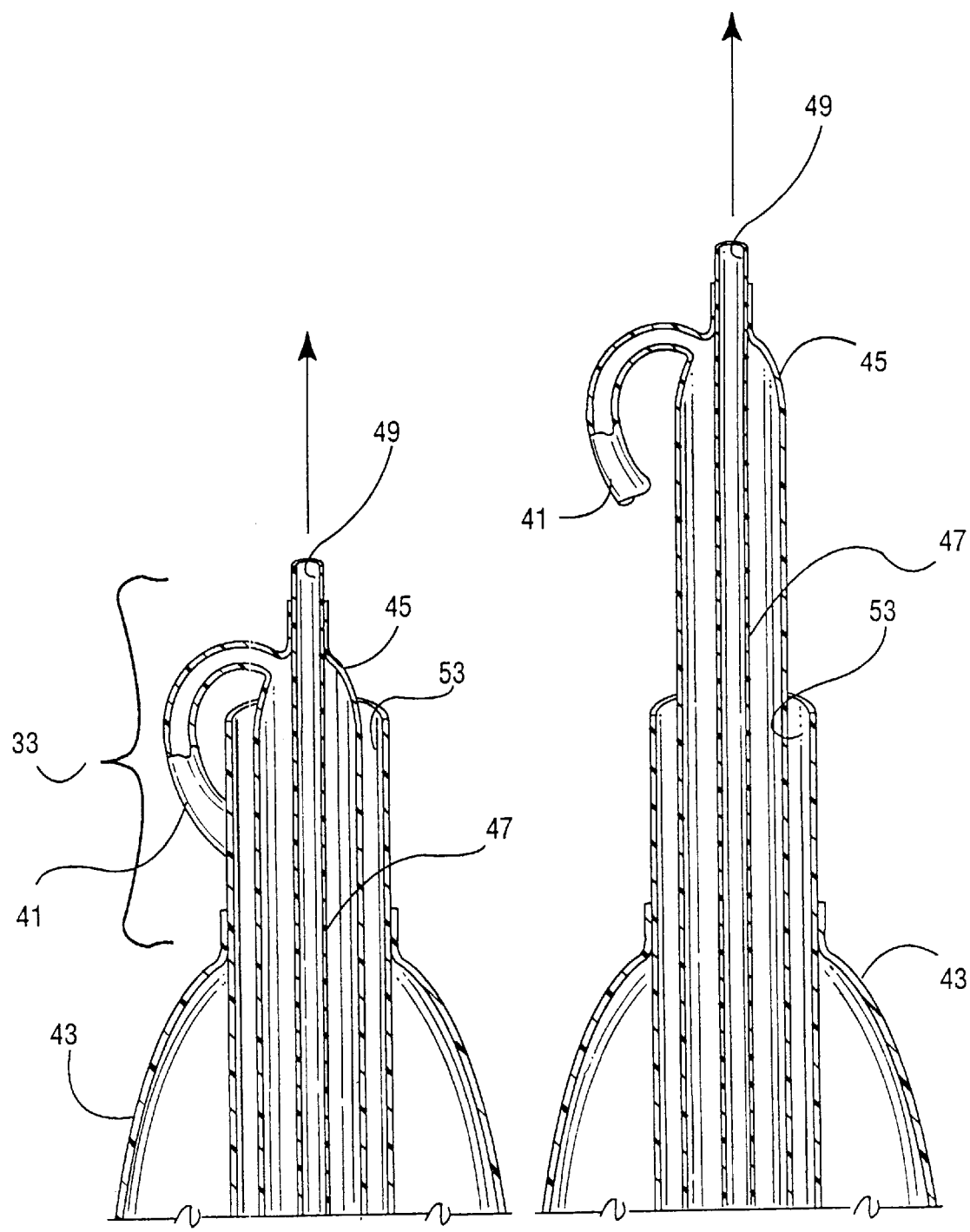
FIG. 5A is cutaway view of the proximal blocking balloon positioned within an inner bore.
FIG. 5B is a cutaway view of the proximal blocking balloon being pushed forward the second stage of insertion.

FIGS. 5A and 5B show in greater detail the parts of the apparatus that allow its positioning within the aorta. The extendable-semirigid tube 47 that runs longitudinally through the apparatus (proximal blocking balloon 45, pumping balloon 43, and lumen sheath 59) is encompassed by an inner bore of support tube 53 as shown in FIG. 5A and 5B. The inner bore of tube 53 serves to house the proximal blocking balloon 45 while the apparatus is in the insertion position. The proximal blocking balloon is slidably coupled within inner bore of 53 to allow movement into the extended position. FIG. 5A and 5B show the apparatus being placed from the non-extended position to a partially-extended position. The proximal blocking balloon 45, being slidably coupled within the inner bore of tube 53, can be moved in the direction of the arrows. This allows the medical practitioner to position the proximal blocking balloon by applying pressure in the direction of the arrow through the pressure control port 55, port 55 being continuous with extendable-semirigid tube 47 which runs longitudinally from the proximal 33 to the distal 35 end of the apparatus, and ultimately extending outside the patient's body.

FIGS. 6A and 6B show how the pressurizable support means 41 is pressurized to support and expand the inside wall of the aorta. The pressurizable support means can be pressurized, and hence expanded, to a support and expansion position within the aorta by a pressurized gas. In the pressurized position, the pressurizable support means makes complete circumferential contact against the inside wall of the aorta, the embodiment shown in FIGS. 2–8 being in the shape of a helical coil. It is to be understood that various other geometries would also function as a pressurizable support means to support and expand the walls of the aorta and simultaneously present a central opening that forms volume 69. The internal profile of the pressurizable support means presents a central opening that forms volume 69, thus allowing blood to flow through the aorta when the pumping balloon is deflated and for the positioning of the other elements. The pressurizable support means can be further pressurized to expand the aorta to help draw blood from the left ventricle of the patient into the aorta and throughout the patient's circulatory system. This expansion of the pressurizable support means is designed to further the function of the other elements of the apparatus, which is to temporarily replace the function of the left ventricle in a patient whose heart is severely injured and is unable to maintain a systemic arterial pressure adequate to support the inside walls of a patient's aorta during the depressurization of the pumping balloon of the invention.

Typically, the systemic pressure within the aorta is 120 mmHg at systole and 80 mmHg at diastole. However, in a severely injured or diseased heart, the blood pressure can drop as low as 40 mmHg. At this pressure or below, the heart is essentially non-functioning and the aorta will collapse on an IABP during its depressurized phase. Thus, currently available IABP devices are only functional when the mean systemic blood pressure is at least 60 mmHg. Once the walls of the aorta collapse due to low blood pressure, presently available IABPs will not operate. The pressurizable support means of the present invention allows use of an IABP at much lower pressures than previous capabilities due to the mechanical support offered by the support means. Further, expansion of the aorta by the support means during depressurization of the pumping balloon provides an additional sucking action to move blood from the left ventricle to the aorta. Finally, the entire apparatus is removable, adding to its wider utility in treating patients for severe heart disease or trauma.

Operation of the Apparatus

The operation of the device will now be described. After positioning the apparatus within the aorta of the patient, it is then capable of performing its function as described in FIGS. 6A through 9. The apparatus has two primary functional modes: the sucking mode, which assists the failing heart while it is in its systolic phase, and the pumping mode, which assists while the failing heart is in its diastolic phase.

Sucking Mode

FIG. 6A, FIG. 6B, and FIG. 7 show the apparatus in its depressurized or sucking functional mode. FIG. 6A and FIG. 6B show the apparatus (the distal end portion 35 shown exclusively in FIG. 6B) inserted within the aorta of a patient with the following functional positions: pumping balloon 43 is in the sucking position (depressurized); proximal blocking balloon 45 in the blocking position (pressurized); pressurizable support means 41 is in the supporting and expanding (pressurized) position; and the blocking balloon 61 is in the blocking position (pressurized).

The pumping balloon is controlled independently of the other inflatable elements (e.g., proximal blocking balloon) through separate and distinct gas carrying means: tube 65 controlling gas pressurization of the pumping balloon and tube 63 controlling gas pressurization of the proximal blocking balloon, as well as the support means 41 and distal blocking balloon 61. The pressurizable support means is in a pressurized expansion position when the blocking balloons are in their blocking positions. The proximal blocking balloon 45 makes firm contact at 57 with the upper portion of the aortic arch 17, and is supported in that position by the strength of the extendable-semirigid tube 47.

By depressurizing, hence deflating, the pumping balloon 43 as shown in FIG. 6A, and simultaneously pressurizing the support means in FIG. 6A, the apparatus draws oxygenated blood from the left ventricle into the volume 69 surrounding the pumping balloon. This creates a volume 69 of low blood pressure such that the walls of the aorta could collapse if not supported by the pressurizable support means 41. Thus, while the pumping balloon is in its deflated sucking state, the support means 41 is pressurized and expanded. Simultaneous to this, the proximal blocking balloon is pressurized to its blocking position to block the aortic arch arteries. The purpose of this is to keep blood within the aortic arch arteries from back-flowing into volume 69, thus forcing blood within the failing heart 29 into volume 69. The blocking balloon 61 is inflated in order to block the retrograde flow of blood from the distal descending aorta, thus strengthening the sucking effect of the pumping balloon in its sucking position.

FIG. 6B shows details of the distal 35 end of the apparatus. Specifically, the tube 63 is coupled to the bottom end 79 of the blocking balloon, which is coupled to the pressurizable support means at the top end 81 of the balloon. Pressurization gas from 39 is pumped into and out of the distal blocking balloon, pressurizable support means, and the proximal blocking balloon through tube 63. The lumen sheath 59 is coupled to the pumping balloon and extends distally to encase tube 65 and the extendable-semirigid tube 47, which becomes port 55. The tube 65 carries the pressurization gas into and out of the pumping balloon.

Ultimately, the port 55, and tubes 63 and 65 extend outside of the aorta and patient's body, the port and tubes being encased within the tube sheath 37. Once outside the body, the individual tubes separate to be coupled to the pressure transducer (port 55) and the pressurization control means (tubes 63, 65).

FIG. 7 shows a cross-sectional view of the aorta and apparatus as taken along line VIII—VIII FIG. 6A. The cross-sectional view shows the proximal blocking balloon 45 in the blocking position. The pressurizable support means 41 is inflated to its expansion position, while the proximal blocking balloon is fitted firmly against the upper portion 57 of the inside wall of the aortic arch 17 portion of the aorta.

Pumping Mode

Figures 8A, 8B, 9:
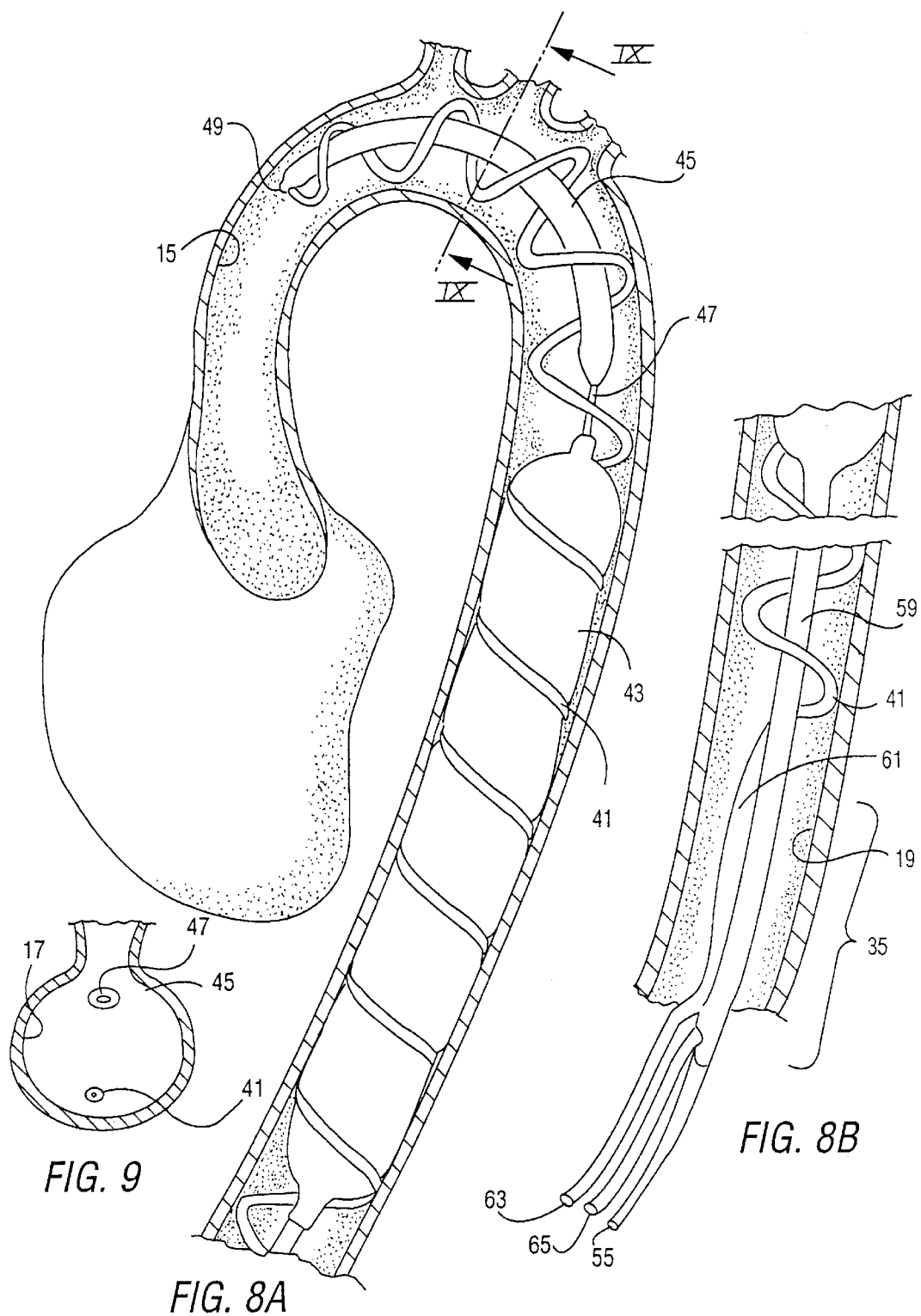
FIG. 8A is a cutaway view of the apparatus within the aorta of a patient, the pumping balloon in the pressurized pumping position.
FIG. 8B is a cutaway view of the distal blocking balloon of the device in the depressurized deflated position.
FIG. 9 is a cross-section taken from FIG. 8A at IX—IX showing the depressurized deflated position of the proximal blocking balloon.

FIG. 8A, FIG. 8B, and FIG. 9 show the inserted apparatus in its pumping functional mode. These figures depict the following functional positions of the elements of one embodiment of the invention: pumping balloon 43 is in the pumping position (pressurized); proximal blocking balloon 45 is in the deflated position (depressurized); pressurizable support means 41 maintained in a depressurized condition; and the distal blocking balloon 61 is in the deflated position (depressurized). Inflation of the pumping balloon 43 to the position shown in FIG. 8A displaces the extendable-semirigid tube toward the center of the aorta and moves the proximal blocking balloon away from the orifices of the aortic arch arteries as illustrated in FIG. 8A and FIG. 9. This facilitates flow from the aorta into the aortic arch arteries.

The pumping balloon is pressurized to expand to a pumping position to fill the volume 69. This forces oxygenated blood towards the aortic arch arteries and the ascending aorta 15 where the coronary ostiums are located. The proximal blocking balloon 45 in its deflated position allows blood to flow into the aortic arch arteries. Further, blood is forced down the descending aorta 19 to supply blood to the lower portion of the patient's body. FIG. 9 is a cross-sectional view of the apparatus and aorta taken along lines IX—IX in FIG. 9A. FIG. 9 shows the deflated position of the proximal blocking balloon 45, and the depressurized condition of the pressurizable support means.

The coupling of the proximal blocking balloon, the support means, and the distal blocking balloon is such that when the pressurizing gas is withdraw through line 63, the larger volume blocking balloon and proximal blocking balloons deflate to a resting (depressurized) position, while the support means is under a lower pressure.

Advantages

The present invention offers many distinct advantages over commonly used LVADs. The present invention can be implemented as easily as the intra-aortic balloon pump devices currently used since it does not require surgically opening the chest and operating on major blood vessels. Therefore, the present invention has the potential for wider application than currently used devices. The present invention can be used in patients that have more severe left ventricular failure than the present IAPBs. In fact, the present invention is designed to completely replace, temporarily, the function of the left ventricle without extensive surgery. Like existing intra-aortic balloon pumps, the present device can be removed without opening the chest and operating on the heart and aorta. If the ventricle does not recover function adequate to sustain life without the continued help of the present invention, it may support the heart until cardiac transplantation can be arranged. Therefore, by utilizing the present invention, additional patients will survive without requiring immediate cardiac transplantation, and for the cases who ultimately require cardiac transplantation, the operation can be done without the complications resulting from prior surgical implantation of a LVAD.

The pressurizable support means of the present invention has a distinct function and advantage relative to stent devices used in body lumen. Stent devices are typically designed to be permanently placed within the lumen, and in particular, lumen smaller than the aortic arch and descending aorta. Further, many of the prior art stents used to expand the walls of lumen must be implanted through surgical procedures. The present invention can be placed within the aorta of the patient through the use of a catheter, thus being less time consuming, and requiring less expertise. Further, the pressurizable support means of the present invention is designed to support the aorta during the sucking phase of the pumping balloon operation when the lowered blood pressure would otherwise cause the aorta to collapse.

While the invention has been shown in only one of its forms, it is not thus limited but is susceptible to various changes and modifications without departing from the spirit thereof.

What is claimed is:

1. A method of temporarily replacing the function of the heart in a patient whose heart is severely injured and is unable to maintain a systemic arterial pressure adequate to support the inside walls of patient's aorta, the method comprising:
    positioning a pressurizable support means within the aortic arch and descending portion of the aorta, the support means having a depressurized position and a pressurized, supporting and expanding position; and
    drawing blood from the left ventricle by pressurizing the pressurizable support means thus expanding the inside walls of the aorta.

2. The method of claim 1, wherein the pressurizable support means is removable, having an external profile which is expandable to fit firmly against the inside wall of the aorta of the patient.

3. The method of claim 1, wherein the pressurizable support means presents a central opening that allows blood to flow through the aorta.

4. The method of claim 1, wherein the pressurizable support means presents a central opening that allows a blood pressure control means to be placed within opening.

5. The method of claim 1, wherein the pressurizable support means is formed in the shape of a coil.

6. The method of claim 1, wherein the pressurizable support means presents a central opening that allows a proximal blocking balloon to be placed within the opening to block the openings to the aortic arch arteries when pressurized.

7. A method of assisting a severely injured heart and supporting the inside wall of a patient's aorta under low blood pressure, the method comprising:
    providing a blood flow control means for supplying a surge of oxygenated blood to the ascending aorta, aortic arch, the coronary arteries and the descending aorta;
    providing a pressurizable support means having an external profile which can be pressurized and depressurized between an insertion position and a supporting position, the pressurizable support means being positionable within the aorta of a patient;
    positioning the pressurizable support means in the insertion position within the aorta of a patient to provide maximal support of the aorta; and
    drawing blood from the left ventricle by pressurizing the pressurizable support means thus expanding the walls of the aorta.

8. The method of claim 7, wherein the pressurizable support means is formed in the shape of a coil.

9. The method of claim 8, wherein the blood flow control means is a pumping balloon located within the coils of the pressurizable support means.

10. The method of claim 9, further comprising a extendable-semirigid tube running longitudinally through the pumping balloon, the extendable-semirigid tube having an inner bore.

11. The method of claim 7, further providing a proximal blocking balloon coupled to the proximal end of the extendable-semirigid tube.

12. The method of claim 11, wherein the proximal blocking balloon can be in either a non-extended position or an extended position within the apparatus.

13. The method of claim 12, wherein the proximal blocking balloon is located within an inner bore in the non-extended position, the outer bore being located within and longitudinal to the pumping balloon.

14. The method of claim 13, wherein the pressurization of the proximal blocking balloon can be controlled independently of the pumping balloon through a separate line.

15. A method of assisting a severely injured heart and supporting the inside wall of a patient's aorta under low blood pressure, the method comprising:
    providing a pressurizable support means having an insertion position and a supporting position, the removable support means being positionable within the aorta of a patient;
    providing a pumping balloon located within the pressurizable support means, the pumping balloon having a pumping position and sucking position;
    providing a proximal blocking balloon located within the coils of the removable support means, the proximal blocking balloon having a deflated position and blocking position;
    coupling the pumping and proximal blocking balloons together through a extendable-semirigid tube;
    positioning the pressurizable support means in the insertion position within the aorta of a patient to provide maximal support of the aorta, and positioning the proximal blocking balloon at the aortic arch;
    pumping blood to the ascending and descending aorta by pressurizing the pumping balloon to the pumping position and simultaneously depressurizing the proximal blocking balloon to a deflated position, simulating systole in a healthy heart; and
    drawing blood from the left ventricle by pressurizing the pressurizable support means and simultaneously depressurizing the pumping balloon to the sucking position and simultaneously pressurizing the proximal blocking balloon to the blocking position to block blood flow from the aortic arch arteries, simulating diastole in a health heart.

16. The method of claim 15, wherein the pressurizable support means is in the shape of a coil.

17. The method of claim 16, wherein the primary and proximal blocking balloons are coupled to one another through a extendable-semirigid tube running longitudinally through the primary and proximal blocking balloons.

18. The method of claim 15, wherein the proximal blocking balloon is located within an inner bore in its non-extended position, the inner bore located within and longitudinal to the pumping balloon.

19. The method of claim 15, wherein the pressurizable support means has a proximal end and a distal end, the proximal end being placed towards the ascending aorta.

20. The method of claim 15, further comprising a distal blocking balloon coupled to the pressurizable support means such that inflation of the blocking balloon also inflates the support means.

21. The method of claim 20, wherein the distal blocking balloon has a blocking position when pressurized, and a deflated position when depressurized.

22. The method of claim 21, wherein the distal blocking balloon is in the blocking position when the pumping balloon is in the sucking position.

23. The method of claim 22, wherein the distal blocking balloon is in the deflated position when the pumping balloon is in the pumping position.

24. The method of claim 15, wherein the apparatus is inserted into the aorta of a patient in two stages, the stages comprising a first stage and a second stage.

25. The method of claim 24, wherein the apparatus is in a depressurized and non-extended position when in the first stage of insertion into the aorta of a patient.

26. The method of claim 25, wherein the apparatus is in a depressurized and extended position when in the second stage of insertion into the aorta of a patient.

27. The method of claim 15, wherein the extendable-semirigid tube has a port at its proximal end to measure the blood pressure within the ascending aorta.

28. The method of claim 27, wherein the extendable-semirigid tube port can be used for the injection of substances into the aorta of the patient.

* * * * *